United States Patent [19]

Horodysky

[11] Patent Number: 4,599,191

[45] Date of Patent: Jul. 8, 1986

[54] FRICTION REDUCING ADDITIVES AND COMPOSITIONS THEREOF

[75] Inventor: Andrew G. Horodysky, Cherry Hill, N.J.

[73] Assignee: Mobil Oil Corporation, New York, N.Y.

[21] Appl. No.: 605,742

[22] Filed: May 1, 1984

[51] Int. Cl.$^4$ .......................................... C10M 137/08
[52] U.S. Cl. .................................. 252/32.5; 252/49.9; 558/177
[58] Field of Search ........................... 252/32.5, 49.9; 260/925

[56] References Cited

U.S. PATENT DOCUMENTS 3,159,664 12/1964 Bartlett ........................... 252/32.7 E
3,979,308 9/1976 Mead et al. ...................... 252/32.7 E

*Primary Examiner*—Jacqueline V. Howard
*Attorney, Agent, or Firm*—Alexander J. McKillop; Michael G. Gilman; Howard M. Flournoy

[57] ABSTRACT

Amine, diamine and triamine salts of diol-derived acid phosphates impart excellent friction reducing and antiwear characteristics to lubricant compositions into which they have been incorporated.

21 Claims, No Drawings

FRICTION REDUCING ADDITIVES AND COMPOSITIONS THEREOF

BACKGROUND OF THE INVENTION

This invention relates to lubricant compositions and more particularly, to lubricant compositions comprising oils of lubricating viscosity or greases thereof containing a minor friction reducing and antiwear amount of a hydrocarbyl amine, a hydrocarbyl diamine or a hydrocarbyl triamine salt of a diol-derived acid phosphate.

Considerable work has been done with lubricating oils, mineral and synthetic to enhance their friction reducing properties by modifying them with suitable additives. The use of lubricant additives containing phosphorus has been well documented and widely implemented commercially. These include acid phosphates, phosphites, phosphonates, phosphate esters, metallic dithiophosphates and the like.

Amine compositions have also found wide use as friction reducing additives as exemplified by U.S. Pat. No. 4,328,113 which relates to alkyl amines and diamines and borated adducts of alkyl amine and diamines.

Alcohol-containing additives and their derivatives are also well known for their surfactant and lubricity properties when formulated into lubricating oils and for their water-scavenging characteristics when blended into hydrocarbyl fuels. The use of glycerol monooleate and similar hydroxyl-containing carboxylates have also found wide spread commercial use as lubricant additives. U.S. Pat. Nos. 3,649,358 and 3,889,433 describe some related diols.

U.S. Pat. No. 3,909,214 describes certain fuel additives consisting essentially of an aliphatic monoamine salt of a branched chain alkyl acid ester of orthophosphoric acid in combination with liquid polypropylene.

It has now been discovered that various amine salts of hydrocarbyl diol-derived phosphates (which can also be referred to as diol-derived acid phosphate salts), when blended into lubricants, provide effective multifunctional friction reducing and antiwear activity with potential antirust and anticorrosion properties. Novel compositions disclosed herein are expected to provide exceptional benefits in a variety of synthetic and mineral oil based lubricants and greases. Both the additives, per se, and lubricant compositions containing such additives are, to the best of applicants' knowledge, novel. To the best of our knowledge, neither the compositions nor the additive compounds have been known or previously used as multifunctional friction reducing, antiwear or antirust additives in lubricanting oils, greases or fuels.

SUMMARY OF THE INVENTION

This invention is more particularly directed to lubricant compositions containing small additive concentrations of amine, diamine or triamine salts of acid phosphates derived from hydrocarbyl diols which exhibit excellent friction reducing properties. Concentrations as little as 1% in fully formulated synthetic and mineral oil based formulations reduce the coefficient of friction by approximately 48% and thus improve lubricity. Significant syngeristic antiwear activity is anticipated from the modest phosphorus content of this highly surface active additive. Antirust and anticorrosion properties are expected, especially for additives derived from ether amines or diamines because of the contained amine moiety.

This invention is also directed to additive compositions as described herein and to a method of reducing fuel consumption in internal combustion engines by treating the moving surfaces of the engines with the novel lubricant compositions hereof.

Accordingly, this invention is specifically directed to lubricant compositions comprising a major proportion of an oil of lubricating viscosity or grease prepared therefrom and a minor effective proportion of a friction reducing/antiwear additive selected from the group consisting essentially of a monoamine, diamine or triamine salt of diol-derived acid phosphates wherein the monoamine, diamine or triamine salt of the diol-derived acid phosphates are prepared from the condensation reaction of said acid phosphates with said amines or mixture of said amines, diamines or triamines.

DESCRIPTION OF SPECIFIC EMBODIMENTS

The amines useful in this invention include monoamines, diamines and triamines. Suitable amines include ether amines such as hydrocarbyloxy-hydrocarbyleneamines, e.g., dodecyloxypropylamine, triisodecyloxypropylamine, etc. Preferred are long chain amines such as oleyl amine, stearyl amine, isostearyl amine, cocamine, tallowamine, hydrogenated tallowamine, t-alkylamines, dodecyl amine, secondary amines such as N-ethyl-oleyl amine, N-methyl-oleyl amine and N-methyl-soya amine. Suitable diamines include ether diamines such as N-hydrocarbyloxy-hydrocarbylene diamines such as N-triisodecyloxypropyl-1,3-propylene diamine, etc. Preferred are diamines such as N-oleyl-1,3-propylene diamine, and N-coco-1-3-propylene diamine. Generally amines having at least 8 to 10 and up to about 29 to 32 carbon atoms including mixtures of such amines have been found to be highly useful in this invention, especially tertiary alkyl amines.

Any suitable diol may be used, however, particularly preferred are 1,2-, 2,3-, 3,4-, 1,3- and 1,4-diols or mixtures thereof. Also included are such diols as alkyl 1,1'-diphenyl-2,2'-diol. Most particularly preferred are long chain vicinal diols having from about 8 to about 18 or more carbon atoms. Suitable polyols having three or more hydroxy groups may also be used. Mixtures of diols can also be used advantageously.

All the reactants used in the process in accordance with this invention can be obtained commercially or made by any convenient means known to the art.

Generally speaking, the process of manufacturing the additives in accordance with this invention may be carried out as follows:

Long chain vicinal diols are (1) converted to their corresponding partial acid phosphates by reaction with phosphorus pentoxide and (2) the acid phosphates are then converted to form the amine salts thereof by reaction with suitable hydrocarbyl amines, diamines or triamines, or hydrocarbyloxy amines, diamines or triamines or mixtures thereof. Solvents can optionally be used in either step of the reaction. A wide temperature range can be used to perform either reaction from as low as room temperature to as high as 150° C. or more, with 60°–100° C. often preferred.

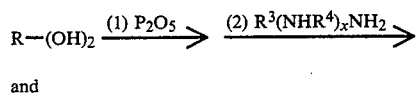

and

R(OH)$_2$ may be 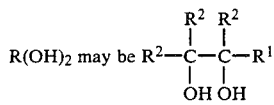

where
- R = C$_{10}$-C$_{48}$ hydrocarbyl
- R$^1$ = C$_8$-C$_{30}$ hydrocarbyl
- R$^2$ = hydrogen or C$_1$-C$_6$ hydrocarbyl
- R$^3$ = C$_8$-C$_{30}$ hydrocarbyl or hydrocarbyloxy hydrocarbylene
- R$^4$ = C$_2$-C$_4$ hydrocarbylene
- x = 0, 1, or 2 or mixtures thereof, as for example, if the resultant product contains a mixture combining product in which x = 1 with product in which x = 2 and giving an average value of 1.5 to x.

The diol or polyol is converted to at least the partial acid phosphate by reaction with 5%-100% molar quantities, preferably 25%-75% molar quantities, of phosphorus pentoxide followed by conversion to the amine salts by reaction with appropriate amounts of the chosen amine, diamine or triamine. Preferably, the amine and the acid phosphate are reacted in stoichiometric ratios of phosphate to amine of from about 3:1 to about 1:3. An excess of amine can be used in this step or a small amount of free acidity can be left by undercharging the amine or the mixtures of amines.

The lubricants contemplated for use herein include both mineral and synthetic hydrocarbon oils of lubricating viscosity, mixtures of mineral and synthetic oils and greases prepared therefrom. Typical synthetic oils are: polypropylene, polypropylene glycol, trimethylol propane esters, neopentyl and pentaerythritol esters, di(2-ethyl hexyl) sebacate, di(2-ethyl hexyl) adiptate, dibutyl phthalate, polyethylene glycol di(2-ethyl hexanoate), fluorocarbons, perfluoro-alkyl-polyethers, silicate esters, silanes, esters of phosphorus-containing acids, liquid ureas, ferrocene derivatives, hydrogenated mineral oils, chain type polyphenyls, siloxanes, and silicones (polysiloxanes) fluorosilicones, alkyl-substituted diphenyl ethers typified by a buty-substituted bis(p-phenoxy phenyl) ether, and phenoxy phenyl ethers.

Other synthetic hydrocarbon oils include hydrocarbon polymers having improved viscosity indices, which polymers are prepared by polymerizing an olefin, or mixture of olefins, having from 5 to 18 carbon atoms per molecule in the presence of an aliphatic halide and a Ziegler-type catalyst.

The amount of additive in the lubricant compositions may range from 0.1 to about 10% by weight of the total lubricant composition. Preferred is from about 0.5 to 5 wt. %. Other additives which may be present include polyalkyl succimide and polyalkenyl ester dispersants, metallic (calcium or magnesium) sulfonates or phenates, metallic or non-metallic phosphorodithioates, polymeric viscosity index improvers and other additives commonly used in lubricants.

Having described the invention in general terms, the following are offered to specifically illustrate this development. It is to be understood that they are illustrations only and that the invention is not thereby limited except as by the appended claims.

The following examples are typical of the preparation of and the additive compounds useful herein. The test data in Tables 1 and 2 below serves to demonstrate their effectiveness in lubricant compositions for reducing friction and conserving energy.

EXAMPLE 1

Partial Acid Phosphate of 1,2-Mixed-Pentadecanediol-Octadecanediol

Approximately 480 g of 1,2-mixed-pentadecanediol-octadecanediol (obtained commercially and containing approximately 28% 1,2-pentadecanediol, 28% 1,2-hexadecanediol, 28% 1,2-heptadecanediol and 16% 1,2-octadenanediol) and 200 g hexane were charged to a 2 liter reactor equipped with agitator and condenser. The contents were warmed to ~60° C. and 70 g phosphorus pentoxide was slowly added over a period of two hours while maintaining a temperature of ~60°-70° C. The temperature was held for one hour at ~60° C. and raised to 100° C. for three additional hours. The remaining solvent was removed by distillation under reduced pressure.

EXAMPLE 2 t-Alkylamine Salt of Partial Acid Phosphate of 1,2-Mixed-Pentadecandiol-Octadecanediol Approximately 135 g of the product of Example 1 was reacted with 50 g of t-alkylamines (in the C$_{11-14}$ range having the following grouping:

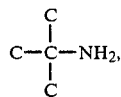

principally t-C$_{11}$H$_{23}$NH$_2$ to t-C$_{14}$H$_{29}$H$_{29}$NH$_2$ having molecular weights of 171-213 and commercially obtained) for ½ hour at 80° C. with agitation until the reaction was complete.

EXAMPLE 3

N-Oleyl-1,3-Propylenediamine Salt of Partial Acid Phosphate of 1,2-Mixed-Pentadecanediol-Octadecanediol Approximately 135 g of the product of Example 1 was reacted with 50 g of n-oleyl-1,3-propylenediamine (commercially obtained) for ½ hour at ~80° C. with agitation until the reaction was complete.

EXAMPLE 4

Acid Phosphate of 1,2-Mixed-Pentadecanediol-Octadecanediol Concentrate in Process Oil Approximately 480 g of 1,2-mixed-pentadecanediol-octadecanediol (as described in Example 1) and 200 g hexane were charged to a 2 liter reactor equipped with agitator and condenser. The contents were warmed to ~60° C. and 140 g phosphorus pentoxide was slowly added over a period of two hours. This temperature was maintained at ~60°-65° C. for one hour and then raised to 100° C. for three additional hours. Approximately 200 g of 100 second solvent parafinic neutral lubricating oil was added at this point as a diluent oil to reduce the viscosity of the intermediate. The remaining solvent was removed by distillation under reduced pressure.

EXAMPLE 5 t-Alkylamine Salt of Partial Acid Phosphate of 1,2-Mixed Pentadecanediol-Octadecanediol Approximately 125 g of the product of Example 4 was reacted with 100 g of the t-alkylamine described in Example 2 for ½ hour at 80° C. with agitation until the reaction was complete.

EXAMPLE 6

N-Oleyl-1,3-Propylenediamine Salt of Acid Phosphate of 1,2-Mixed-Pentadecanediol-Octadecanediol Approximately 135 g of the product of Example 4 was reacted with 95 g of N-oleyl-1,3-propylenediamine for ½ hour at 80° C. with agitation until reaction was complete.

Certain of the acid phosphate amine salts as described herein was blended into fully formulated synthetic and mineral oil based engine oil lubricants and evaluated using the Low Velocity Friction Apparatus Test. The formulations included polymeric dispersants, metallic phenates, metallic sulfonates, zinc phosphorodithioate and viscosity index improving additives. The use of only 1.0% of the product of Example 3 reduced the coefficient of friction by 48% as shown in Table 1. These additives appear to be exceptionally effective friction reducers.

EVALUATION OF PRODUCTS

LOW VELOCITY FRICTION APPARATUS

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces are submerged in the test lubricant. Friction between the steel surfaces is measured as a function of the sliding speed at a lubricant temperature of 250° F. The friction between the rubbing surfaces is measured using a torque arm-strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infinitely variable-speed hydraulic transmission driven by a ½ HP electric motor. To vary the sliding speed, the output speed of the transmission is regulated by a lever-cam motor arrangement.

Procedure

The rubbing surfaces and 12–13 ml of test lubricant are placed on the LVFA. A 240 psi load is applied, and the sliding speed is maintained at 40 fpm at ambient temperature for a few minutes. A plot of coefficients of friction ($U_k$) over the range of sliding speeds, 5 to 40 fpm (25–195 rpm), is obtained. A minimum of three measurements is obtained for each test lubricant. Then, the test lubricant and specimens are heated to 250° F., another set of measurements is obtained, and the system is run for 50 minutes at 250° F., 240 psi and 40 fpm sliding speed.

Freshly polished steel specimens are used for each run. The surface of the steel is parallel ground to 4–8 microinches.

The data obtained are shown in Tables 1 and 2. The percentages by weight are percentages by weight of the total lubricating oil composition, including the usual additive package. The data are percent decrease in friction according to:

$$\frac{(U_k \text{ of oil alone}) - (U_k \text{ of additive plus oil})}{(U_k \text{ of oil alone})} \times 100$$

The value for the oil alone would be zero for the form of the data shown in the Tables.

TABLE 1

| Friction Test Results Using Low Velocity Friction Apparatus | | |
|---|---|---|
| | Additive Conc. in Test Oil | % Reduction in Coefficient of Friction at |
| | Weight % | 5 Ft/Min 30 Ft/Min |
| Base Fluid A (fully formulated mineral oil based automotive engine oil containing detergent/dispersant/inhibitor performance package) SAE 10W40 | — | 0    0 |
| Example 2 - t-Alkylamine salt of partial acid phosphate of 1,2-mixed- pentadecane diol-octadenanediol | 1.0 | 17   21 |
| Example 3 - N—Oleyl-1,3-propylenediamine salt of partial acid phosphate of 1,2-mixed-pentadecanediol-octadecanediol | 1.0 | 48   37 |
| Example 6 - N—Oleyl-1,3-Propylenediamine salt of acid phosphate of 1,2-mixed-pentadecanediol-octadecanediol | 1.0 | 15   16 |

TABLE 2

| Friction Test Results Using Low Velocity Friction Apparatus | | |
|---|---|---|
| | Additive Conc. in Base Fluid | % Reduction in Coefficient of Friction at |
| | Weight % | 5 Ft/Min 30 Ft/Min |
| Base Fluid B (fully formulated synthetic oil based automotive engine oil containing detergent/dispersant/inhibitor performance package) SAE 5W30 | — | 0    0 |
| Example 2 - t-Alkylamine salt of partial acid phosphate of 1,2-mixed-pentadecane-diol-octadecanediol | 1.0 | 28   21 |
| Example 3 - N—Oleyl-1,3-propylenediamine salt of partial acid phosphate of 1,2-mixed-pentadecanediol-octadecanediol | 1.0 | 9    9 |
| Example 6 - N—Oleyl-1,3-propylenediamine salt of acid phosphate of 1,2-mixed-pentadecanediol-octadecanediol | 1.0 | 5    11 |

The above data clearly demonstrates that additive amounts of the diol-derived acid phosphate amine salts is premium quality automotive and industrial lubricants significantly enhance the lubricants energy efficiency, antiwear and antirust characteristics. The unique additives dscribed in this patent application are useful at low concentrations, are non-metallic and do not contain any potentially corrosive sulfur. These salts can be readily prepared in a one pot process similar to many reactions currently practiced in an attractive commercial basis.

It is understood that those of ordinary skill in the art that departure from the preferred embodiments described herein can be effective made and that such departures within the scope of the specification.

What is claimed is:

1. A lubricant composition comprising a major proportion of an oil of lubricating viscosity or grease prepared therefrom and a minor effective proportion of a friction reducing additive consisting of monoamine, diamine or triamine salts or mixtures thereof of diol-derived acid phosphates wherein said diol is a long chain vicinal diol having the following general structure:

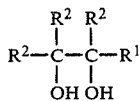

where
$R^1 = C_8-C_{30}$ hydrocarbyl
and $R^2 =$ hydrogen or $C_1-C_6$ hydrocarbyl
and wherein said amines have the following general structure;

where $R^3 = C_8-C_{10}$ hydrocarbyl or hydrocarbyloxy hydrocarbylene, $R^4 = C_2-C_4$ hydrocarbylene and $x = 0, 1,$ or $2$.

2. The composition of claim 1 wherein the diol-derived acid phosphate is converted to at least a partial acid phosphate by reaction with from about 5 to about 100% molar quantities of phosphorus pentoxide.

3. The composition of claim 1 wherein said additive is a tertiary-alkyl amine salt of a partial acid phosphate of 1,2-mixed-pentadecanediol-octadecanediol where the alkyl moiety has from about 11 to about 14 carbon atoms.

4. The composition of claim 1 wherein said additive is the N-oleyl-1,3-propylene diamine salt of partial acid phosphate of 1,2-mixed-pentadecanediol-octadecanediol.

5. The composition of claim 1 wherein said additive is the N-oleyl-1,3-propylene diamine salt of acid phosphate of 1,2-mixed-pentadecanediol-octadecanediol.

6. The composition of claim 1 wherein said oil of lubricating viscosity is a mineral oil or fractions thereof or a synthetic oil or a mixture of mineral and synthetic oils.

7. The composition of claim 6 wherein said oil of lubricating viscosity is a mineral oil.

8. The composition of claim 3 wherein said oil of lubricating viscosity is a mineral oil.

9. The composition of claim 4 wherein said oil of lubricating viscosity is a mineral oil.

10. The composition of claim 5 wherein said oil of lubricating viscosity is a mineral oil.

11. The composition of claim 6 wherein said oil of lubricating viscosity is a synthetic oil.

12. The composition of claim 3 wherein said oil is a synthetic oil.

13. The composition of claim 4 wherein said oil is a synthetic oil.

14. The composition of claim 5 wherein said oil is a synthetic oil.

15. The composition of claim 1 wherein said major proportion is a grease.

16. The composition of claim 3 wherein said major proportion is a grease.

17. The composition of claim 4 wherein said major proportion is a grease.

18. The composition of claim 5 wherein said major proportion is a grease.

19. The composition of claim 1 containing from about 0.1 to about 10 weight percent of said additive.

20. The composition of claim 19 containing about 2 to about 4 weight percent of said additive.

21. An amine, diamine or triamine salt of a diol-derived acid phosphate prepared by reacting a diol or mixtures thereof having the following general formula:

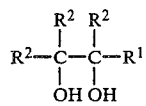

where
$R^1 = C_8-C_{30}$ hydrocarbyl
and $R^2 =$ hydrogen or $C_1-C_6$ hydrocarbyl
with phosphorus pentoxide under suitable conditions of time, temperature and pressure to provide at least a partial acid phosphate thereof and thereafter reacting the resultant acid phosphate with a hydrocarbyl or hydrocarbyloxy hydrocarbylene amine or mixtures thereof having the following general structure:

where $R^3 = C_8-C_{10}$ hydrocarbyl or hydrocarbyloxy hydrocarbylene, $R^4 = C_2-C_4$ hydrocarbylene and $x = 0, 1,$ or $2$.

* * * * *

UNITED STATES PATENT AND TRADEMARK OFFICE
CERTIFICATE OF CORRECTION

PATENT NO. : 4,599,191

DATED : July 8, 1986

INVENTOR(S) : Andrew G. Horodysky

It is certified that error appears in the above-identified patent and that said Letters Patent is hereby corrected as shown below:

Column 3, line 44, "buty-substituted" should be --butyl-substituted--.

Column 4, line 36, "t-$C_{14}H_{29}H_{29}NH_2$" should be --t-$C_{14}H_{29}NH_2$--.

Column 5, line 19, "was" should be --were--.

Signed and Sealed this

Thirteenth Day of January, 1987

*Attest:*

DONALD J. QUIGG

*Attesting Officer*　　*Commissioner of Patents and Trademarks*